Figure 1:
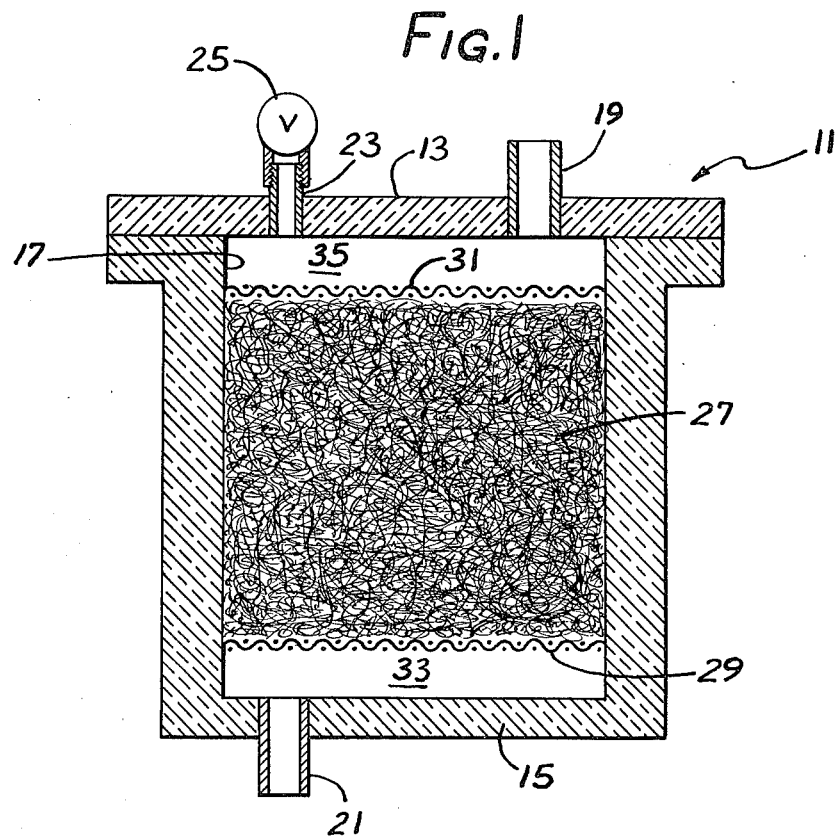

United States Patent
Bokros

[11] 3,972,818
[45] Aug. 3, 1976

[54] BLOOD FILTER USING GLASSY CARBON FIBERS

[75] Inventor: Jack C. Bokros, San Diego, Calif.

[73] Assignee: General Atomic Company, San Diego, Calif.

[22] Filed: Aug. 22, 1974

[21] Appl. No.: 499,505

[52] U.S. Cl............................ 210/435; 210/505; 210/DIG. 23
[51] Int. Cl.² ........................................ B01D 27/00
[58] Field of Search ............... 117/106 R, 106 C; 210/435, 436, 500–508, DIG. 23; 252/444

[56] References Cited
UNITED STATES PATENTS

| | | | |
|---|---|---|---|
| 3,441,142 | 4/1969 | Oja | 210/500 X |
| 3,448,401 | 6/1969 | Swank | 210/DIG. 23 |
| 3,593,854 | 7/1971 | Swank | 210/DIG. 23 |
| 3,677,795 | 7/1972 | Bokros | 117/106 C |
| 3,795,088 | 3/1974 | Esmond | 210/DIG. 23 |
| 3,811,927 | 5/1974 | Joo | 117/106 R |

Primary Examiner—Charles N. Hart
Assistant Examiner—Richard W. Burks
Attorney, Agent, or Firm—Fitch, Even, Tabin & Luedeka

[57] ABSTRACT

A device for treating human blood prior to its return to a living human body. The blood filter employs a bed of fibers between about 1 and 100 microns in diameter, the outer surface of which is formed of impermeable carbon. Suitable fibrous substrates may be coated with vapor-deposited pyrolytic carbon, and the fibers may be supported between upper and lower screens which are likewise coated.

1 Claim, 2 Drawing Figures

BLOOD FILTER USING GLASSY CARBON FIBERS

This invention relates to the filtration of blood and more particularly to an improved filter for use in a extracorporeal blood circulation circuit.

Various types of blood filters have been developed for use in the extracorporeal circulation of the blood, particularly in connection with a heart-lung machine, with a kidney machine, or with other types of blood-pump or assist devices. Examples of some such blood filters are shown in U.S. Pat. Nos. 3,448,041, and 3,593,854. Blood filters may also be used to filter blood which is being transfused from storage to a living body.

It is the general objective of such blood filters to remove microemboli from blood being returned to a living human being, and a discussion of the potential dangers to a patient which can be alleviated by the use of blood filtering is set forth in an article entitled "Platelet-Leukocyte Emboli — Origins, Effects & Treatment" that appeared in the Fall, 1973 issue of *The Journal of Extra-Corporeal Technology*, Volume V, Number 4, pp. 23–33.

Presently available blood filters are not considered to be entirely satisfactory. Although they have been considered to have been effective to remove certain microemboli from the bloodstream, these filters are also considered to create other problems which are believed to inure from their inherent incompatibility with blood. The disadvantage is that, even though an ideal filter may be designed for the removal of pre-existing microemboli, if thrombogenic materials are used in its construction, the filger can alter the protein and other elements of blood so that emboli are formed downstream of the filter, i.e., the filter itself can be an emboli generator, thus markedly reducing its effectiveness. Accordingly, blood filters designed to achieve the desirable objectives of those presently available and to obviate such disadvantages are desired.

Figure 2:
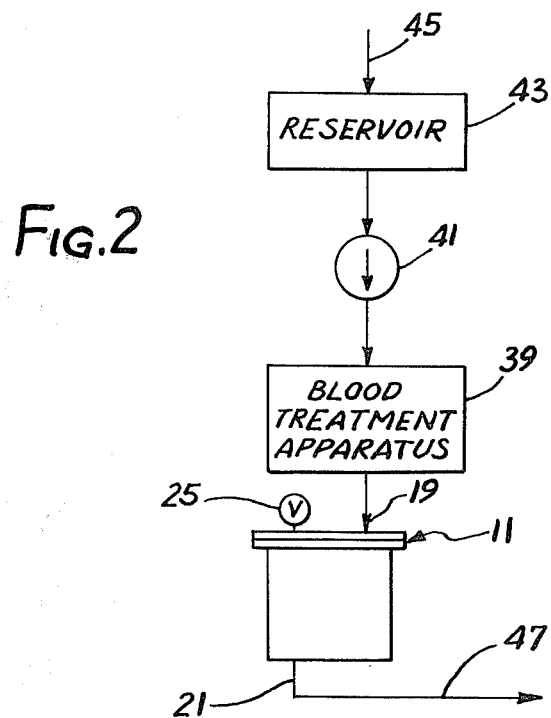

It is an object of the present invention to provide an improved blood filter. It is another object of the invention to provide an effective blood filter having improved compatibility with human blood. A further object of the invention is to provide a method for treating human blood to remove microemboli therefrom in a manner so as not to adversely affect the blood. These and other objects of the invention will be apparent from the following detailed description when read in conjunction with the accompaying drawings wherein:

FIG. 1 is a sectional view through a blood filter embodying various features of the invention; and FIG. 2 is a diagrammatic view illustrating a blood treatment system which utilizes the blood filter shown in FIG. 1.

It has been found that, by utilizing a bed of fibers having an impermeable carbon surface, a filter device can be constructed which does an excellent job of removing undesirable debris and microemboli from blood. However, because of the inherent compatibility of impermeable carbon with the components of human blood, a filter constructed in this manner causes no adverse effects in blood being so treated and reduces the rate of nucleation of new emboli downstream of the filter.

Show in FIG. 1 is an illustrative blood filter 11 which includes a housing made from an upper cap 13 and a lower body 15. The illustrated housing is formed from glass, and the two parts 13, 15 are suitably joined together at their interface by adhesive or by suitable mechanical means so as to create an internal, closed chamber 17 of a chamber 17 of a general cylindrical shape, the horizontal cross-section of which chamber is circular. Instead of forming the housing parts from glass, a suitable metal such as stainless steel could be used, in which case interior chamber-forming surface would be coated with impermeable vapor-deposited carbon.

An entrance conduit 19 is provided in the upper cap 13 of the housing, and an exit conduit 21 is provided in the lower body 15. A vent conduit 23 is also provided in the cap of the housing to which a suitable check valve 25 can be attached which will permit the escape of air or other gases from the chamber 17 while precluding flow thereinto in the opposite direction.

The filtration effect of the blood filter 11 is performed by a bed of carbon fibers 27 which are supported within the chamber 17 between a lower screen 29 and an upper screen 31. Instead of screens, other porous grid materials, e.g., lattices of fused glass frit, which are nonthrombogenic can be used. The screens 29, 31 are suitably held in place either adhesively, or by any other suitable means, for example, by grooving the internal wall of the chamber 17. The lower screen 29 is spaced from the bottom of the chamber 17 a sufficient distance to create a lower plenum 33 wherein the filtered blood can collect and flow smoothly to the exit conduit 21. The upper screen 31 is preferably also spaced slightly below the top of the chamber 17, creating an upper plenum 35 so that the incoming blood can be fed to the entire upper horizontal surface of the fiber bed 27. The screens 29 and 31 are made of suitable materials which are compatible with blood, such as stainless steel wire that has been coated with vapor-deposited impermeable carbon.

The carbon fiber bed which effects the filtering is made up of fibers 27 having at least an outer impermeable carbon surface. Pyrolytic carbon is created by the thermal destruction of a carbon-containing compound, usually a hydrocarbon, in vapor form; however, carbon coatings can also be deposited by vapor-deposition without such destruction by using ion-plating or the like, as where a carbon atmosphere is created under very low pressure conditions using, for example, electron beam heating. For purposes of this application, such vapor deposited carbon is considered to be impermeable if it has density equal to at least about 70% of its theoretical maximum density (or at least about 1.55 grams per cm$^3$ for substantially pure carbon). Glassy or vitreous carbon is inherently impermeable and may be employed at slightly lower densities, and fibers made solely of such carbon are commercially available in the United States. The size of the carbon fibers 27 may vary between about 1 micron and about 100 microns in diameter; however, preferably, fibers between about 5 and about 50 microns in diameter are employed. Fibers in this size range provide a tortuous path through which the blood must flow to traverse the filter from the inlet 19 to the outlet 21, and undesirable microemboli are removed as the blood flows along this tortuous path. The length of the fibers will depend somewhat upon the processing method. The fibers should preferably be at least 0.1 inch (.25 cm) in length.

The fibers 27 can be totally glassy carbon in the aforementioned size range, or they may be made from fine fibers of suitable material which have been coated with pyrolytic or nonpyrolytic carbon by a vapor deposition process. It may be important that the fiber surfaces are smooth, and tumbling or the like may be used to remove surface roughness from coated fibers. Inasmuch as the fine fibrous substrates will be totally encapsulated within the impermeable carbon, any suitable material can be employed which is stable at the temperatures at which the vapor deposition coating will take place. If pyrolytic carbon is to be used for the coatings, the deposition temperatures may be between 1200° and 2000°C. Fine zirconium oxide and silicon carbide fibers are readily commercialy available and are often employed; however, other refractory materials, such as silica and alumina, may be used when depositing pyrolytic carbon coatings. The crystalline character of the carbon coating is not considered to be of particular significance, and both laminar carbons and isotropic carbons, which can be vapor-deposited at relatively low temperatures, e.g., 900° to 1600°C., are considered to perform satisfactorily. When vacuum vapor deposition or ion-plating is used, high temperature stability is no longer a criterion, and glass fibers or organic polymer fibers can be used.

FIG. 2 depicts one illustrative system wherein the blood filter 11 might be employed. Diagrammatically illustrated is a blood treatment apparatus 39, which might be a heart-lung machine or the like. The heart-lung machine 39 would be fed with blood by suitable blood pump 41 which draws its suction from a reservoir 43. The reservoir 43 has an inlet line 45 which may be connected to the human body from which the blood is being drawn; however, the line 45 might also be branched to provide for a subsidiary supply of blood from a blood bank, should it be needed. The heart-lung machine 39 would discharge the blood to the entrance 19 to the blood filter 11, wherein the blood would percolate downward through the carbon fiber bed 27. The filtered blood leaves through the outlet 21 and is returned to the human body through the line 47, driven by the pressure head supplied by the pump 41.

The illustrated blood filter 11 is made from a glass body 15 wherein a chamber 17 is formed, the internal diameter of which measures about 3 inches. The chamber 17 includes a bed of carbon-coated fibers 27 having a depth of about 2 inches. The fibers are made of 10-micron diameter silicon carbide substrates which have been coated with an outer coating of vapor-deposited pyrolytic carbon, the thickness of the coating averaging about 25 microns. The fine fibrous substrates are coated using a mixture of methane and argon at atmospheric pressure (about 10 volume percent methane) and at a temperature of about 1100°C. to produce laminar pyrolytic carbon having a B.A.F. of 5 and a density of about 2 grams per $cm^3$. The coatings are smooth in the as-deposited condition, so no further treatment is necessary.

The coated fibers range in size from about 50 microns to about 75 microns in diameter, and about 0.25 cm. to about 1.27 cm. in length, and they are supported upon a lower screen of stainless steel wire coated with vapor-deposited carbon having screen openings measuring about 50 microns. The upper screen 31 is made of similar material and is formed to have openings of about 75 microns. Accordingly, the upper screen serves to remove relatively large emboli aggregates from the incoming bloodstream, for example, those over 200 microns in size, leaving the carbon fiber bed to remove the remaining microemboli. The blood filter 11 is, of course, designed to be a disposable item which would not be reused after the operation with a particular patient is completed.

Although the invention has been described with regard to a blood filter of one particular construction, it should be understood that modifications as would be obvious to one having the ordinary skill of the art may be made without deviating from the scope of the invention which is set forth in the appended claims. For example, the vapor-deposited pyrolytic carbon which is employed to coat the fibrous substrates, the screens, and perhaps the interior of the blood filter chamber, may be alloyed with a minor amount of a carbide-forming metal or metalloid, for example, silicon, to give added strength to the carbon surface, in a manner that is known in the coating art. Additional features of the invention are set forth in the claims which follow.

What is claimed is:

1. A disposable device for treating human blood prior to its return to a particular, single living human body, which device comprises a housing having a chamber formed therein, entrance means and exit means communicating with said chamber, and a bed of fibers disposed in said chamber so that a liquid must pass through said bed in order to travel from said entrance to said exit, said fiber bed being made up of individual fibers between about 1 micron and about 100 microns in diameter, said individual fibers being formed of impermeable glassy carbon, which glassy carbon constitutes the outer surface of said fibers.

* * * * *